US006545134B1

(12) United States Patent
Eschenmoser et al.

(10) Patent No.: US 6,545,134 B1
(45) Date of Patent: Apr. 8, 2003

(54) METHOD FOR THE PRODUCTION OF PENTOPYRANOSYL NUCLEOSIDES

(75) Inventors: Albert Eschenmoser, Küsnacht (CH); Stefan Pitsch, Zürich (CH); Sebastian Wendeborn, Binningen (CH)

(73) Assignee: Nanogen Recognomics, GmbH., Frankfurt (DE)

( * ) Notice: Subject to any disclaimer, the term of this patent is extended or adjusted under 35 U.S.C. 154(b) by 0 days.

(21) Appl. No.: 09/647,829

(22) PCT Filed: Apr. 7, 1999

(86) PCT No.: PCT/EP99/02356

§ 371 (c)(1),
(2), (4) Date: Jan. 18, 2001

(87) PCT Pub. No.: WO99/52923

PCT Pub. Date: Oct. 21, 1999

(30) Foreign Application Priority Data

Apr. 8, 1998 (DE) .......................... 198 15 901

(51) Int. Cl.[7] .......................... C07H 15/00; C07H 17/00
(52) U.S. Cl. .................. 536/17.3; 536/17.2; 536/18.5; 536/18.6; 536/18.7; 536/27.3; 536/27.6; 536/28.53
(58) Field of Search ................ 536/18.6, 18.7, 536/18.5, 27.3, 27.6, 28.53, 17.2, 17.3

(56) References Cited

U.S. PATENT DOCUMENTS 5,624,802 A  4/1997  Urdea et al.
5,632,957 A  5/1997  Heller et al.

FOREIGN PATENT DOCUMENTS

WO  WO 89/02439  3/1989
WO  WO 93/20242  10/1993
WO  WO 99/15540  4/1999

OTHER PUBLICATIONS

Pitsch et al., Helvetica Chimica Acta, vol. 76, pp. 2161–2183, 1993.*
Pitsch et al, "Pyranosyl–RNA ('p–RNA') : Base Pairing Selectivity and Potential to Replicate", Helvetica Chimica Acta, vol. 78 (1995), pp. 1621–1635.
Krishnamurthy et al, Angew Chem. 1996, 108, No. 13/14, pp. 1619–1622.
Mirkin et al, "A DNA–based Method for Rationally Assembling Nanoparticles Into Macroscopic Materials", Nature, vol. 382, 1996, pp. 607–609.
Alivisatos et al, "Organization of Nanocrystal Molecules Using DNA", Nature, vol. 382, 1996, pp. 609–611.
Lombardi et al, "De Novo Design of Heterotrimeric Coiled Coils", pp. 495–504, 1996.
Mickey S. Urdea, "Branched DNA Signal Amplification", Bio/Technology vol. 12, 1994, pp. 926–928.

Bird et al, "Single–Chain Antigen–Binding Proteins", 1998, pp. 423–426.
Huston et al, "Protein Engineering of Antibody Binding Sites: Recovery of Specific Activity in an Anti–Digoxin Single–Chain $F_v$ Analogue Produced in *Escherichia coli*", Proc. Natl. Acad. Sci. USA, vol. 85, 1988, Biochemistry, pp. 5879–5883.
Fodor et al, "Multiplexed Biochemical Assays with Biological Chips", Nature, vol. 364, 1993, pp. 555–556.
Southern et al, "Analyzing and Comparing Nucleic Acid Sequences by Hybridization to Arrays of Oligonucleotides: Evaluation Using Experimental Models", Genomics, 13, 1992, pp. 1008–1017.
Zhu et al, "Preparation of Vitamin $B_6$–Conjugated Peptides at the Amino Terminus and of Vitamin $B_6$–Peptide–Oligonucleotide Conjugates", Bioconjugate Chem, 1994, vol. 5, pp. 312–315.
Aketa et al, "Stereochemical Studies. $Xt^{l)}$ A Biomimetic Conversion of $_L$–Lysine into Optically Active 2–Substituted Piperidines. Syntheses of D–and L Pipecolic Acid, and (S) (+)–Coniine from $_L$–Lysine$^{2)}$"; Chem. Pharm. Bull. 24(4), 1976, pp. 621–631.
Nelson et al, Nucleic Acids Research, vol. 17, No. 18, 1989.
Hayakawa et al, "The Allylic Protection Method in Solid Phase Oligonucleotide Synthesis. An efficient Preparation of Solid–Anchored DNA Oligoners", J. Am. Chem. Soc. vol. 112, 1990, pp. 1691–1696.
N.N. Suvorov et al, Biol. Aktivn. Soedin., Akad. Nauk SSSR, 60, (1965).
Balaban et al, "Stability and Equilibria of Free Radicals–III", Tetrahedron, vol. 23, pp. 4661–4676, 1967.
Jeanloz et al, "1,5–Anhydroribitol", vol. 70, pp. 4052–4054.
Mullis et al, "Specific Synthesis of DNA in Vitro via a Polymerase–Catalyzed Chain Reaction", Methods in Enzymology. vol. 155, pp. 335–350.
Better et al, "*Escherichia Coli* Secretion of an Active Chimeric Antibody Fragment", Science, vol. 240, pp. 1041–1043.
Plückthun et al, "Assembly of a Functional Immunoglobulin $F_v$ Fragment in *Escherichia Coli*", Science, vol. 240, pp. 1038–1041.
Y.V. Dobriynin et al, Khim–Farm. Zh. 12, 33 (1978).
Kuehne et al, J. Org. Chem. Vol. 43, No. 13, 1978, pp. 2733–2735.
A. Giannis et al, Angew Chem. 101 No. 2, 1989, pp. 220–222.
Fissekis et al, "Synthesis of 5–Hydroxyalkylpyrimidines from Lactones", J. Org. Chem. vol. 29, 1964, pp. 2670–2673.
Fissekis et al, "The Chemistry of Some 5–(2–Hydroxyalkyl) Uracil Derivatives and a Synthesis of 5–Vinyluracil", J. Org. Chem. vol. 28, No. 2, 1973.

(List continued on next page.)

*Primary Examiner*—James O. Wilson
(74) *Attorney, Agent, or Firm*—O'Melveny & Myers LLP

(57) ABSTRACT

Processes for the preparation of 3′,4′-cyclic acetals of pentopyranosylnucleosides, in which the pentopyranosyl nucleoside is reacted with an aldehyde, ketone, acetal, or ketal under reduced pressure of less than about 500 mbar.

31 Claims, 6 Drawing Sheets

OTHER PUBLICATIONS

Vorbrüggen et al, "Nucleoside Synthesis with Trimethylsilyl Triflate and Perchlorate as Catalysts", Chem. Ber. 114, 1234–1255 (1981), also referred to as XP 002121064.

Pitsch et al, "Why Pentose and Not Hexose–Nucleic Acids?", 1993, also referred to as XP 002094190, pp. 2161–2183.

Böhringer et al, "Warum Pentose–und Nicht Hexose–Nucleinsäuren?", Helvetica Chimica Acta, vol. 75, 1992, pp. 1416–1476.

Chemical Reviews, Uhlmann et al, "Antisense Oligonucleotides: A New Therapeutic Principle", vol. 90, No. 4, Jun. 1990;

* cited by examiner

METHOD FOR THE PRODUCTION OF PENTOPYRANOSYL NUCLEOSIDES

The present invention relates to a process for the preparation of a 3',4'-cyclic acetal of a pentopyranosylnucleoside, in which a pentopyranosylnucleoside is reacted with an aldehyde, ketone, acetal or ketal under reduced pressure.

Pyranosylnucleic acids (p-NAs) structural types which are in general isomeric to the natural RNA, in which the pentose units are present in the pyranose form and are repetitively linked by phosphodiester groups between the positions C-2' and C-4' (FIG. 1). In this context, "nucleobases" are understood as meaning the canonical nucleobases A, T, U, C, G, but also the pairs isoguanine/isocytosine and 2,6-diaminopurine/xanthine and, within the meaning of the present invention, also other purines and pyrimidines. p-NAs, namely the p-RNA's derived from ribose were described for the first time by Eschenmoser et al. (see. S. Pitsch et al., Helv. Chim. Acta 76, 2161 (1993); S. Pitsch et al., Helv. Chim Acta 78, 1621 (1995); Angew. Chem. 108, 1619–1623 (1996)). They form exclusively so-called Watson-Crick-paired, i.e. purine/pyrimidine and purine/purine-paired, antiparallel, reversibly "melting", quasi-linear and stable duplices. Homochiral p-RNA strands of the opposite chiral sense likewise pair controllably and are strictly nonhelical in the duplex formed. This specificity, which is valuable for the construction of supramolecular units, is associated with the relatively low flexibility of the ribopyranose phosphate backbone and with the strong inclination of the base plane to the strand axis and the tendency resulting from this for intercatenary base stacking in the resulting duplex and can finally be attributed to the participation of a 2',4'-cis-disubstituted ribopyranose ring in the construction of the backbone. These significantly better pairing properties make p-NAs pairing systems which are to be preferred, compared with DNA and RNA, for use in the construction of supramolecular units. They form a pairing system which is orthogonal to natural nucleic acids, i.e. they do not pair with the DNAs and RNAs occurring in the natural form, which is of importance, in particular, in the diagnostic field.

Eschenmoser et al. have for the first time prepared a p-RNA, as shown in FIG. 2 and illustrated below (see also S. Pitsch et al. (1993), supra).

In this context, a suitable protected nucleobase was reacted with the anomer mixture of the tetrabenzoylribopyranose by action of bis(trimethylsilyl)acetamide and a Lewis acid such as, for example, trimethylsilyl trifluoromethanesulfonate (analogously to Vorbrüggen, H. et al., Chem. Ber. 114, 1234 (1981)). Under the action of a base (NaOH in THF/methanol/water in the case of the purines; saturated ammonia in MeOH in the case of the pyrimidines), the acyl protective groups were removed from the sugar, and the product was protected in the 3',4'-position with p-anisaldehyde dimethyl acetal under acidic catalysis. The diastereomer mixture was acylated in the 2'-position, and the 3',4'-methoxybenzylidene-protected 2'-benzoate was deacetalated by acidic treatment, e.g. with trifluoroacetic acid in methanol, and was reacted with dimethoxytrityl chloride. The 2'→3' migration of the benzoate was initiated by treatment with p-nitrophenol/4-dimethylaminopyridine/triethyl-amine/pyridine/n-propanol. Almost all reactions were worked up by column chromatography. The key unit synthesized in this way, the 4'-DMT-3'-benzoyl-1'-nucleobase derivative of the ribopyranose, was then partly phosphitylated and bonded to a solid phase via a linker.

In the following automated oligonucleotide synthesis, the carrier-bonded component in the 4'-position was repeated acidically deprotected, a phosphoramidite was coupled on under the action of a coupling reagent, e.g. a tetrazole derivative, still free 4'-oxygen atoms were acetylated and the phosphorus atom was oxidized in order thus to obtain the oligomeric product. The residual protective groups were then removed, and the product was purified and desalted by means of HPLC.

The process described by Eschenmoser et al., however, cannot be reproduced with the yields indicated and is thus hardly suitable for application on the industrial scale.

The object of the present invention was therefore to make available a process which makes possible preparation of pentopyranosylnucleosides on the industrial scale.

It has now surprisingly been found that the preparation of the 3',4'-cyclic acetal of a pentopyranosylnucleoside which is an intermediate in the Eschenmoser synthesis only takes place in appreciable yields if the pentopyranosylnucleoside is reacted with an aldehyde or ketone or with an acetal or ketal under reduced pressure.

One subject of the present invention is therefore a process for the preparation of a 3',4'-cyclic acetal of a pentopyranosylnucleoside, in which a pentopyranosylnucleoside is reacted with an aldehyde, ketone, acetal or ketal under reduced pressure.

The term reduced pressure is understood according to the present invention as meaning, in particular, a pressure of less than about 500 mbar, preferably of less than about 100 mbar, in particular of less than about 50 mbar, especially of about 30 mbar.

The aldehyde is, for example, formaldehyde, acetaldehyde, benzaldehyde or 4-methoxybenzaldehyde, the acetal is formaldehyde dimethyl acetal, acetaldehyde dimethyl acetal, benzaldehyde dimethyl acetal or 4-methoxybenzaldehyde dimethyl acetal, the ketone is acetone, cyclopentanone or cyclohexanone and the ketal is acetone dimethyl ketal, cyclopentanone dimethyl ketal, cyclohexanone dimethyl ketal or is in the form of 2-methoxypropene.

In a particular embodiment, the pentopyranosylnucleoside is purified before the reaction, for example on $SiO_2$, preferably on $SiO_2$ in the form of silica gel. Purification on a silica gel chromatography column, for example, is suitable for this. A gradient of about 1–20% or about 5–15% of methanol in dichlormethane, for example, is suitable for the elution of the pentopyranosylnucleoside. It is particularly advantageous if the pentopyranosylnucleoside is neutralized before the purification, for example with a 1% strength hydrochloric acid solution or with solid ammonium chloride, and the solvents are optionally stripped off.

A suitable pentopyranosylnucleoside is in general a ribo-, arabino-, lyxo- or xylo-pyranosylnucleoside. Examples of suitable pentopyranosylnucleosides are a pentopyranosylpurine, -2,6-diaminopurine, -6-purinethiol, -pyridine, -pyrimidine, -adenosine, -guanosine, -isoguanosine, -6-thioguanosine, -xanthine, -hypo-xanthine, -thymidine, -cytosine, -isocytosine , -indole, -tryptamine, -N-phthaloyl-tryptamine, -uracil, -caffeine, -theobromine, -theophylline, -benzotriazole or -acridine.

By way of formula, the pentopyranosylnucleosides can be represented by the formula (I)

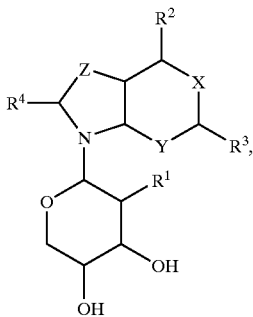

(I)

in which
R$^1$ is equal to H, OH or Hal where Hal is equal to Br or Cl,
R$^2$, R$^3$ and R$^4$ independently of one another, identically or differently, are in each case H, Hal where Hal is equal to Br or Cl, NR$^5$R$^6$, OR$^7$, SR$^8$, =O, C$_n$H$_{2n+1}$ where n is an integer from 1–12, preferably 1–8, in particular 1–4, or (C$_n$H$_{2n}$)NR$^{10}$, R$^{11}$ where R$^{10}$, R$^{11}$ are equal to H, C$_n$H$_{2n+1}$ or R$^{10}$R$^{11}$ is a radical of the formula (III)

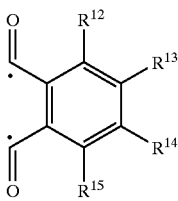

in which R$^{12}$, R$^{13}$, R$^{14}$ and R$^{15}$ independently of one another, identically or differently, are in each case H, OR$^7$, where R$^7$ has the meaning mentioned, or C$_n$H$_{2n+1}$, or C$_n$H$_{2n+1}$, where n has the abovementioned meaning, and
R$^5$, R$^6$, R$^7$ and R$^8$ independently of one another, identically or differently, are in each case H, C$_n$H$_{2n+1}$, or C$_n$H$_{2n-1}$, where n has the abovementioned meaning, —C(O)R$^9$ where R$^9$ is equal to a linear or branched, optionally substituted alkyl or aryl radical, preferably a phenyl radical,
X, Y and Z independently of one another, identically or differently, are in each case =N—, =C(R$^{16}$)— or —N(R$^{17}$)— where R$^{16}$ and R$^{17}$ independently of one another, identically or differently, are in each case H or C$_n$H$_{2n+1}$ or (C$_n$H$_{2n}$)NR$^{10}$R$^{11}$ having the abovementioned meanings,
or by the formula (II)

(II)

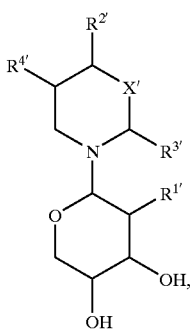

in which R$^{1'}$ is equal to H, OH or Hal where Hal is equal to Br or Cl,
R$^{2'}$, R$^{3'}$ and R$^{4'}$ independently of one another, identically or differently, are in each case H, Hal where Hal is equal to Br or Cl, =O, C$_n$H$_{2n+1}$ or OC$_n$H$_{2n-1}$, or (C$_n$H$_{2n}$)NR$^{10'}$R$^{11'}$, where R$^{10'}$, R$^{11'}$, independently of one another, have the abovementioned meaning of R$^{10'}$ and R$^{11'}$, and
X' in each case is =N—, =C(R$^{16'}$)— or —N(R$^{17'}$)—, where R$^{6'}$ and R$^{17'}$ independently of one another have the abovementioned meaning of R$^{16}$ and R$^{17}$.

The process according to the invention is in general carried out at a temperature of about 40–70° C., preferably of about 50–60° C., in particular of about 50–55° C. Furthermore, the reaction is in general carried out under acidic catalysis, for example in the presence of p-toluenesulfonic acid, methanesulfonic acid, tetrafluoroboric acid, sulfuric acid, acidic ion exchangers, such as, for example, acidic Amberlite® (Rohm & Haas) and/or Lewis acids, such as, for example, zinc chloride, trimethylsilyl triflate or pyridinium paratoluene sulfonate. The reaction times are customarily about 1–1.5 hours, preferably about 1.5 hours.

In a further embodiment of the process according to the invention, in a further step the 3',4'-cyclic acetal of a pentopyranosylnucleoside obtained according to the above process can be protected in the 2' position. The 2' position is preferably protected by a protective group which is base-labile or can be removed by metal catalysis, in particular by an acyl group, especially by an acetyl, benzoyl, nitrobenzoyl and/or methoxybenzoyl group, according to processes known to the person skilled in the art, for example with benzoyl chloride in a dimethylamino-pyridine/pyridine solution at room temperature.

In a further embodiment of the process according to the invention, the 3',4'-cyclic acetal of a pentopyranosylnucleoside protected in the 2' position can be deketalized. In general, the deketalization is carried out in the presence of an acid, preferably in the presence of a strong acid, such as, for example, trifluoroacetic acid. The working-up of the reaction product obtained is preferably carried out under dry basic conditions, for example in the presence of solid hydrogen-carbonate, carbonate and/or basic ion exchanger, such as, for example, basic Amberlite® (Rohm & Haas). The worked-up reaction product can then be purified, for example, on SiO$_2$, in particular on SiO$_2$ in the form of silica gel.

In a further embodiment of the process according to the invention, in a further step the 4' position can also be protected. A suitable protective group is in general an acid- or base-labile protective group, preferably a trityl group, in particular a DMT group, and/or a β-eliminable group, in particular an Fmoc group. The introduction of a protective group is carried out according to generally known processes, for example by means of dimethoxytrityl chloride in the presence of, for example, N-ethyldiisopropylamine (Hünig's base).

In a further embodiment of the process according to the invention, in a further step a rearrangement of the protective group from the 2' position to the 3' position can be carried out. In general, the rearrangement is carried out in the presence of a base, in particular in the presence of N-ethyldiisopropylamine and/or triethylamine according to generally known processes, e.g. in the presence of a mixture of N-ethyldiisopropylamine, isopropanol, p-nitrophenol and dimethylaminopyridine in pyridine, at elevated temperature, e.g. about 60° C. The products obtained can then be purified by means of chromatography on SiO$_2$, in particular on SiO$_2$ in the form of silica gel, and/or crystallization.

The starting compound for the described process according to the invention, the pentopyranosylnucleoside, can be prepared, for example, by first reacting a protected nucleobase with a protected ribopyranose and then removing the protective groups from the ribopyranosylmoiety. The process can be carried out, for example, as described in Pitsch et al. (1993), supra, or Pitsch et al. (1995), supra. To avoid further time- and material-consuming chromatography, it is advantageous here to employ only anomerically pure protected pentopyranoses, such as, for example, tetrabenzoylpentopyranoses, preferably □-tetrabenzoyl ribopyranoses (R. Jeanloz, J. Am. Chem. Soc. 1948, 70, 4052).

Another subject of the present invention is therefore also a process for the preparation of a ribopyranosylnucleoside, in which (a) a protected nucleobase is reacted with a protected ribopyranose, (b) the protective groups are removed from the ribopyranosylhnoiety of the product from step (a) and (c) the product from step (b) is reacted according to the process according to the invention described above in greater detail.

For the preparation of a pentopyranosylnucleic acid, the pentopyranosylnucleoside obtained is either phosphitylated in a further step for oligomerization or bonded to a solid phase for solid-phase synthesis. The phosphitylation is carried out, for example, by means of allyl N-diisopropylchlorophosphoramidite in the presence of a base, e.g. N-ethyldiisopropylamine. The bonding of a protected pentopyranosylnucleoside according to the invention to a solid phase, e.g. long-chain alkylamino controlled pore glass (CPG, Sigma Chemie, Munich) can be carried out, for example, as described in Pitsch et al. (1993), supra.

Another subject of the present invention therefore relates to a process for the preparation of a pentopyranosylnucleic acid, in which (a) in a first step a pentopyranosylnucleoside is prepared according to the process according to the invention described above, (b) in a second step the pentopyranosylnucleoside prepared according to step (a) is bonded to a solid phase, and (c) in a further step the pentopyranosylnucleoside bonded to a solid phase according to step (b) is extended by a phosphitylated 3', 4'-protected pentopyranosylnucleoside, and (d) step (c) is repeated with identical or different phosphitylated 3', 4'-protected pentopyranosylnucleosides until the desired pentopyranosylnucleoside is obtained.

In a particular embodiment, in step (b) and/or step (c) the pentofuranosyl-nucleosides customary in the generally known nucleic acid synthesis can also be incorporated, such as, for example, the adenosine, guanosine, cytidine, thymidine and/or uracil occuring in its natural form (see, for example, Uhlmann, E. & Peyman, A. (1990). Chemical Reviews, 90, 543–584 No. 4), by means of which a mixed nucleic acid made of pentopyranosylnucleosides and pentofuranosyl-nucleosides having novel properties is formed.

Coupling reagents employed for the extension according to step (c) are in general acidic activators, preferably 5-(4-nitrophenyl)-1H-tetrazole, in particular benzimidazolium triflate, as with benzimidazolium triflate, in contrast to 5-(4-nitrophenyl)-1H-tetrazole as a coupling reagent, no blockage of the coupling reagent lines and contamination of the product takes place.

Furthermore, it is advantageous by addition of a salt, such as sodium chloride, to the hydrazinolysis removing the protective groups, to protect the nucleobases, in particular pyrimidine bases, especially uracil and thymine, against ring opening which would destroy the oligonucleotide. Allyloxy groups can preferably be removed, for example, before hydrazinolysis by palladium [Pd(0)] complexes.

The removal of the nucleic acid formed from the solid phase is in general also carried out by hydrazinolysis.

In a further embodiment according to the invention, in a further step (e) the protective groups and the pentopyranosylnucleic acid formed are therefore removed from the solid phase.

In general, the pentopyranosylnucleic acids prepared according to the invention are purified by chromatography, for example on alkylsilylated silica gel, preferably on RP-$C_{18}$ silica gel.

FIG. 3 provides an exemplary general view of the process according to the invention including further embodiments.

The pentopyranosylnucleic acids prepared according to the invention are suitable, for example, for the preparation of pairing systems or conjugates.

Pairing systems are supramolecular systems of noncovalent interaction, which are distinguished by selectivity, stability and reversibility, and whose properties are preferably influenced thermodynamically, i.e. by temperature, pH and concentration. On account of their selective properties, such pairing systems can be used, for example, also as "molecular adhesive" for the bringing together of different metal clusters to give cluster associates having potentially novel properties [see, for example, B. R. L. Letsinger, et al., Nature 1996, 382, 607–9; P. G. Schultz et al., Nature 1996, 382, 609–11]. Consequently, the p-NAs are also suitable for use in the field of nanotechnology, for example for the production of novel materials, diagnostics and therapeutics and also microelectronic, photonic or optoelectronic components and for the controlled bringing together of molecular species to give supramolecular units, such as, for example, for the (combinatorial) synthesis of protein assemblies [see, for example, B. A. Lombardi, J. W. Bryson, W. F. DeGrado, Biomoleküls (Pept. Sci.) 1997, 40, 495–504], as p-NAs form pairing systems which are strongly and thermodynamically controllable. A further application therefore results, especially in the diagnostic and drug discovery field, due to the possibility of providing functional, preferably biological, units such as proteins or DNA/RNA sections with a p-NA code which does not interfere with the natural nucleic acids (see, for example, WO 93/20242).

In addition, a biomolecule, e.g. DNA or RNA, can be used for noncovalent bonding (linking) to another biomolecule, e.g. DNA or RNA, if both biomolecules contain sections which, on account of complementary sequences of nucleobases, can bond to one another by formation of hydrogen bridges. Biomolecules of this type are used, for example, in analytical systems for signal amplification, where a DNA molecule whose sequence is to be analyzed is to be immobilized on a solid support on the one hand via such a noncovalent DNA linker, and on the other hand, is to be bonded to a signal-amplifying branched DNA molecule (bDNA) (see FIG. 3; S. Urdea, Bio/Technol. 1994, 12, 926 or U.S. Pat. No. 5,624,802). A significant disadvantage of the last-described systems is that up to now they are inferior to the processes for nucleic acid diagnosis by polymerase chain reaction (PCR) (K. Mullis, Methods Enzymol. 1987, 155, 335) with respect to sensitivity. Inter alia, this is to be attributed to the fact that the noncovalent bonding of the solid support to the DNA molecule to be analyzed does not always take place specifically, just like the noncovalent bonding of the DNA molecule to be analyzed, owing to which mixing of the functions "sequence recognition" and "noncovalent bonding" occurs. The use of p-NAs as an orthogonal pairing system which does not intervene in the DNA or RNA pairing processes solves this problem in an advantageous manner, owing to which the sensitivity of the analytical processes described can be markedly increased.

Within the meaning of the present invention, conjugates are covalently bonded hybrids of p-NAs and other biomolecules, preferably a peptide, protein or a nucleic acid, for example an antibody or a functional moiety thereof or a DNA and/or RNA occurring in its natural form. Functional moieties of antibodies are, for example, Fv fragments (Skerra & Plückthun (1988) Science 240, 1038), single-chain Fv fragments (scFv; Bird et al. (1988), Science 242, 423; Huston et al. (1988) Proc. Natl. Acad. Sci. U.S.A., 85, 5879) or Fab fragments (Better et al. (1988) Science 240, 1041). In general p-RNA/DNA or p-RNA/RNA conjugates are preferred.

Conjugates are preferably used if the functions "sequence recognition" and "noncovalent bonding" have to be carried out in a molecule, since the conjugates contain two pairing systems which are orthogonal to one another.

The term conjugate within the meaning of the present invention is also understood as meaning so-called arrays. Arrays are arrangments of immobilized recognition species which, especially in analysis and diagnosis, play an important role in the simultaneous determination of analytes. Examples are peptide arrays (Fodor et al., Nature 1993, 364, 555) and nucleic acid arrays (Southern et al. Genomics 1992, 13, 1008; Heller, U.S. Pat. No. 5,632,957). A higher flexibility of these arrays can be achieved by bonding the recognition species to coding oligonucleotides and the associated, complementary strands to specific positions on a solid support. By applying the coded recognition species to the "anticoded" solid support and establishment of hybridization conditions, the recognition species are noncovalently bonded to the desired positions. Owing to this, various types of recognition species, such as, for example, DNA sections, antibodies, can only be arranged simultaneously on a solid support by use of hybridization conditions. As a prerequisite for this, however, codons and anticodons which are extremely strong, selective—in order to keep the coding sections as short as possible—and do not interfere with natural nucleic acid are necessary. p-NAs, preferably p-RNAs, are particularly advantageously suitable for this.

For the preparation of conjugates, both sequential and convergent processes are suitable, convergent processes proving particularly preferred on account of their flexibility.

In a sequential process, after automated synthesis of a p-RNA oligomer has been carried out directly on the same synthesizer, a DNA oligonucleotide, for example, is further synthesized—after adjustment of the reagents and the coupling protocol. This process can also be carried out in the reverse sequence.

In a convergent process, for example, p-RNA oligomers having amino-terminal linkers and, for example, DNA oligomers having, for example, thiol linkers are synthesized in separate processes. An iodoacetylation of the p-RNA oligomer and the coupling of the two units according to protocols known from the literature (T. Zhu et al., Bioconjug. Chem. 1994, 5, 312) is preferably then carried out.

Particularly preferred amino-terminal linkers are allyloxy linkers of the formula (IV)

$$S_{c1}NH(C_nH_{2n})CH(OPS_{c2}S_{c3})C_nH_{2n}S_{c4} \quad (IV),$$

in which $S_{c1}$ and $S_{c4}$ independently of one another, identically or differently, in each case are a protective group, in particular selected from Fmoc and/or DMT, $S_{c2}$ and $S_{c3}$ independently of one another, identically or differently, in each case are an allyloxy and/or diisopropylamino group and n is an integer from 1–12, preferably 1–8, in particular 1–4. A particularly preferred allyloxy linker is 2-(S)-N-Fmoc-$O^1$-DMT-$O^2$-allyloxydiisopropylaminophosphinyl-6-amino-1,2-hexanediol.

2-(S)-N-Fmoc-$O^1$-DMT-$O^2$-allyloxydiisopropylaminophosphinyl-6-amino-1,2-hexanediol can be prepared, for example, from 6-amino-2(S)-hydroxyhexanoic acid. 6-Amino-2(S)-hydroxyhexanoic acid can be prepared from L-lysine by diazotization and subsequent hydrolysis in an manner known from the literature (K.-I. Aketa, Chem. Pharm Bull., 24, 621 (1976)). This is then reacted with FmocCl to give the 2-(S)-N-Fmoc-6-amino-1,2-hexanediol, which can be DM-tritylated according to WO 89/02439 to give the 2-(S)-N-Fmoc-$O^1$-DMT-6-amino-1,2-hexanediol. This is reacted, for example, to give the 2-(S)-N-Fmoc-$O^1$-DMT-$O^2$-allyloxydiisopropylaminophosphinyl-6-amino-1,2-hexanediol in the presence of ethyldiisopropylamine and chloro-N,N-diisopropylaminoallyloxy-phosphine.

Starting from, for example, lysine, it is thus possible in a few reaction steps to synthesize amino-terminal linkers which carry both an activatable phosphorus compound and an acid-labile protective group, such as DMT, and can therefore easily be used in automatable oligonucleotide synthesis (see, for example, B. P. S. Nelson et al., Nucleic Acid Res. 17, 7179 (1989); L. J. Arnold et al., WO 89/02439). A lysine-based linker, in which an allyloxy group is incorporated on the phosphorus atom instead of the otherwise customary cyanoethyl group, can advantageously be employed in the Noyori oligonucleotide method (R. Noyori, J. Am. Chem. Soc. 112, 1691–6 (1990)).

In a further embodiment of the process according to the invention for the preparation of pentopyranosylnucleic acids, in a further step an allyloxy linker of the formula (IV)

$$S_{c1}NH(C_nH_{2n})CH(OPS_{c2}S_{c3})C_nH_{2n}S_{c4} \quad (IV),$$

in which $S_{c1}$ and $S_{c4}$ independently of one another, identically or differently, in each case are a protective group in particular selected from Fmoc and/or DMT, $S_{c2}$ and $S_{c3}$ independently of one another, identically or differently, in each case are an allyloxy and/or diisopropylamino group and n is an integer from 1–12, preferably 1–8, in particular 1–4, is incorporated.

In addition, indole derivatives as linkers, (see, for example, formula (I) in combination with formula (III)) have the advantage of the ability to fluoresce and are therefore particularly preferred for nanotechnology applications in which it may be a matter of the detection of very small amounts of substance. For example, indole-1-ribosides, such as already described in N. N. Suvorov et al., Biol. Aktivn. Soedin., Akad. Nauk SSSR, 60 (1965) and Tetrahedron 23, 4653 (1967), are suitable. In general, 3-substituted derivatives are prepared via the formation of an aminal of the unprotected sugar component and an indoline, which is then converted into the indole-1-riboside by oxidation. For example, indole-1-glucosides and -1-arabinosides (Y. V. Dobriynin et al., Khim.-Farm. Zh. 12, 33 (1978)), were described, whose 3-substituted derivatives can in general be prepared via Vilsmeier reaction.

For the preparation of indole-based linkers, for example, the starting materials used are phthalic anhydride and tryptamine, which are reacted to give N-phthaloyltryptamine (Kuehne et al., J. Org. Chem. 43, 13, 2733–2735 (1987)). This is reduced, for example, to the indoline using borane- THF (analogously to A. Giannis et al., *Angew. Chem.* 101, 220 (1989)). Subsequently, the 3-substituted indoline can be reacted first with ribose to give the nucleoside triol and then with acetic anhydride to give the triacetate. This is then oxidized, for example, with 2,3-dichloro-5,6-dicyanoparaquinone, the acetates are cleaved with, for example, sodium methoxide, benzoylated selectively in the 2' position, DM-tritylated selectively in the 4' position, and the migration reaction to give the 3'-benzoate is carried out. The phosphoramidite is formed according to known processes. This can be employed for automated oligonucleotide synthesis without alteration of the synthesis protocol.

Further linkers suitable for the process according to the invention (see, for example, formula (II) in combination with formula (III)) are uracil-based linkers in which the 5' position of the uracil has been modified. A suitable example is N-phthaloylaminoethyluracil, which can be obtained from hydroxyethyluracil.

The preparation of hydroxyethyluracil is possible on a large scale according to a known method (J. D. Fissekis, A. Myles, G. B. Brown, *J. Org. Chem.* 29, 2670 (1964)). Subsequently, for example, the hydroxyethyluracil obtained is mesylated with methanesulfonyl chloride in pyridine (J. D. Fissekis, F. Sweet, *J. Org. Chem.* 38, 264 (1973)). In general, the reaction product is then reacted with sodium azide in DMF to give the azide and this is reduced with triphenylphosphine in pyridine to the aminoethyluracil. The amino function is finally protected, for example, with N-ethoxycarbonylphthalimide. Nucleosidation of a ribose tetrabenzoate with N-phthaloylaminoethyluracil yields, for example, a ribose tribenzoate linker in good yields. Subsequent removal of the benzoate protective groups with NaOMe in MeOH yields the linker triol, which can be reacted with benzoyl chloride, for example, at −78° C. in pyridine/dichloromethane 1:10 in the presence of DMAP. In addition to the desired 2'-benzoate (64%), 2',4'-dibenzoylated product (22%) is also obtained here, which is collected and can be converted again into the triol. The 2'-benzoate is tritylated in the 4' position in yields of greater than 90%, for example, using dimethoxytrityl chloride in the presence of Hünig's base in dichloromethane. The rearrangement of 4'-DMT-2'-benzoate to 4'-DMT-3'-benzoate is carried out, for example, in the presence of DMAP, p-nitrophenol and Hünig's base in n-propanol/pyridine 5:2. After chromatography, 4'-DMT-3'-benzoate is obtained, which can finally be reacted, for example, with ClP(OAll)N(iPr)$_2$ in the presence of Hünig's base to give the phosphoramidite. This can be employed for automated oligonucleotide synthesis without alteration of the synthesis protocols.

The following figures and examples are intended to describe the invention in greater detail without restricting it.

DEFINITIONS OF THE ABBREVIATIONS

Figure 1:
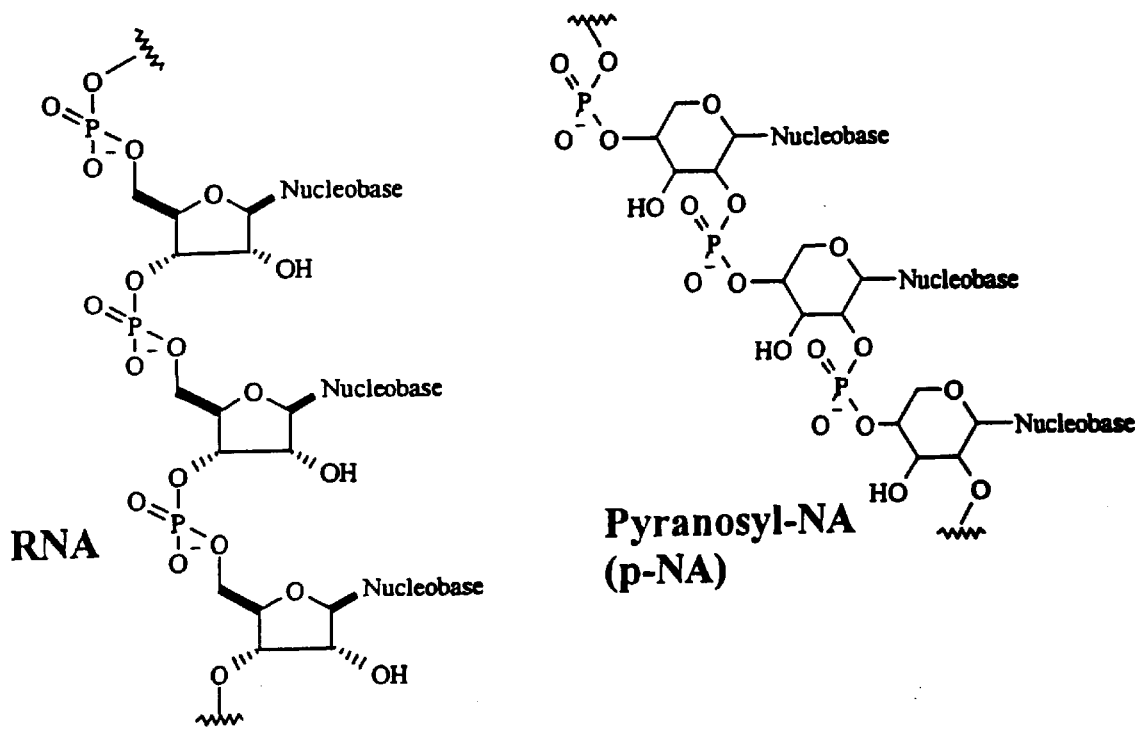
FIG. 1: A diagram showing the differences in the chemical structure of RNA (left) and pyranosyl RNA (right).
Figure 2A:
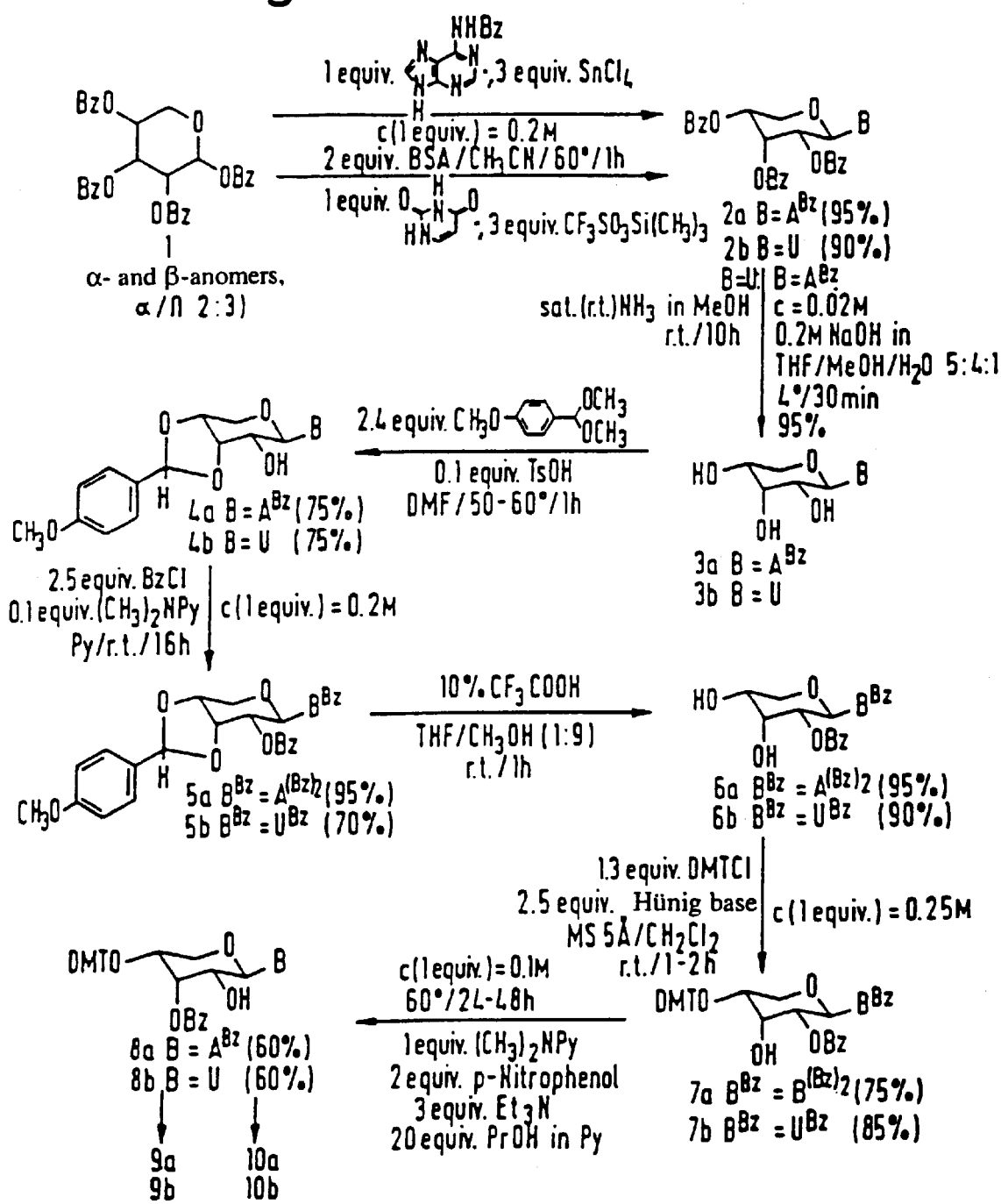
FIGS. 2A and 2B: A reaction scheme showing the Pitsch, et al., (1993) process for the preparation, and phosphitylation or binding to a solid phase, of p-ribo(A or U)-nucleosides.
Figure 2B:
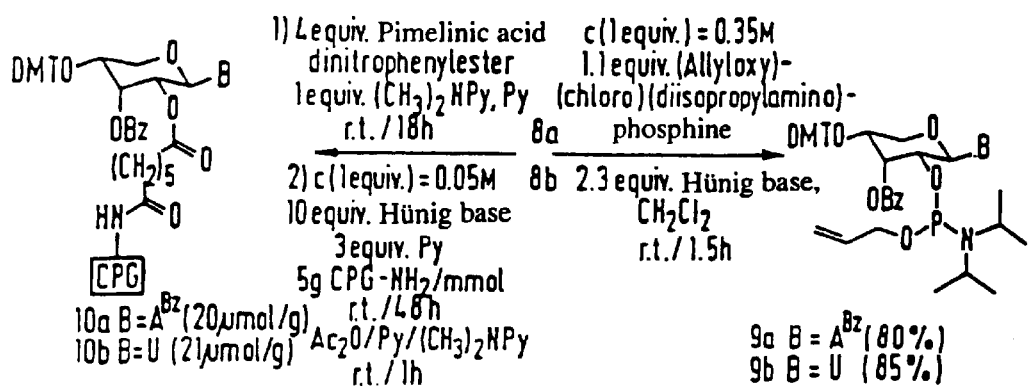
Figure 2B:
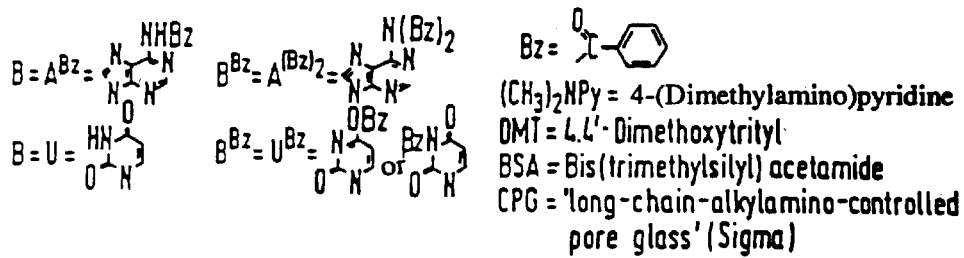
Figure 3A:
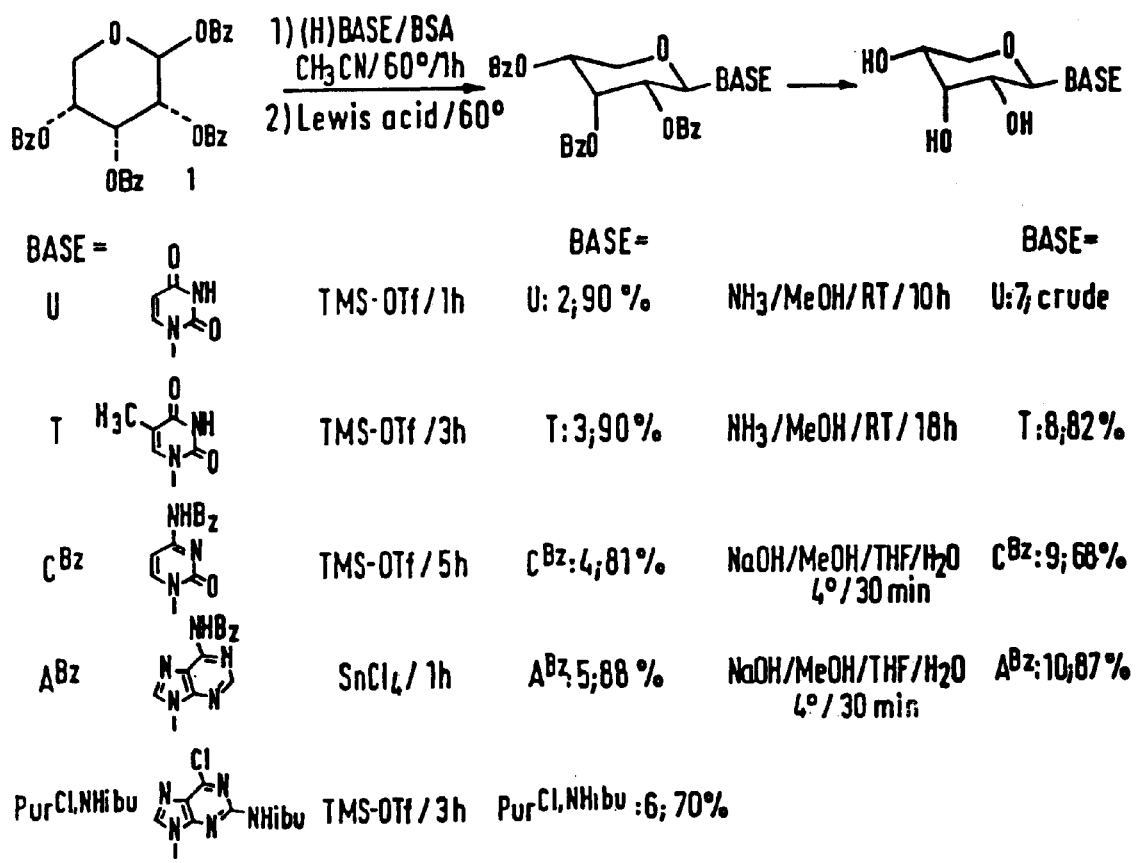
FIG. 3A: A reaction scheme showing the preparation of several unprotected ribopyranosyl nucleosides, in which a protected nucleobase is reacted with a protected ribopyranose.
Figure 3A:
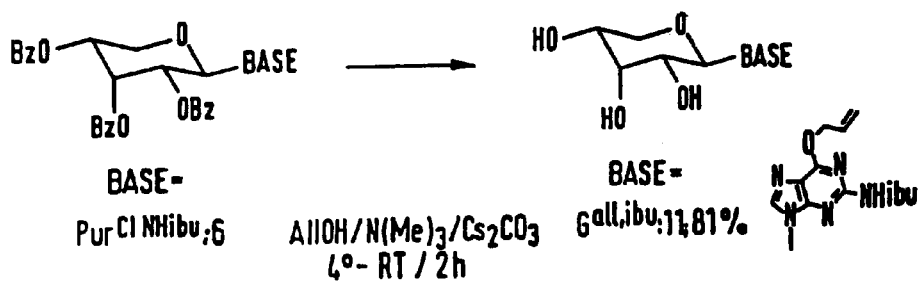
Figure 3B:
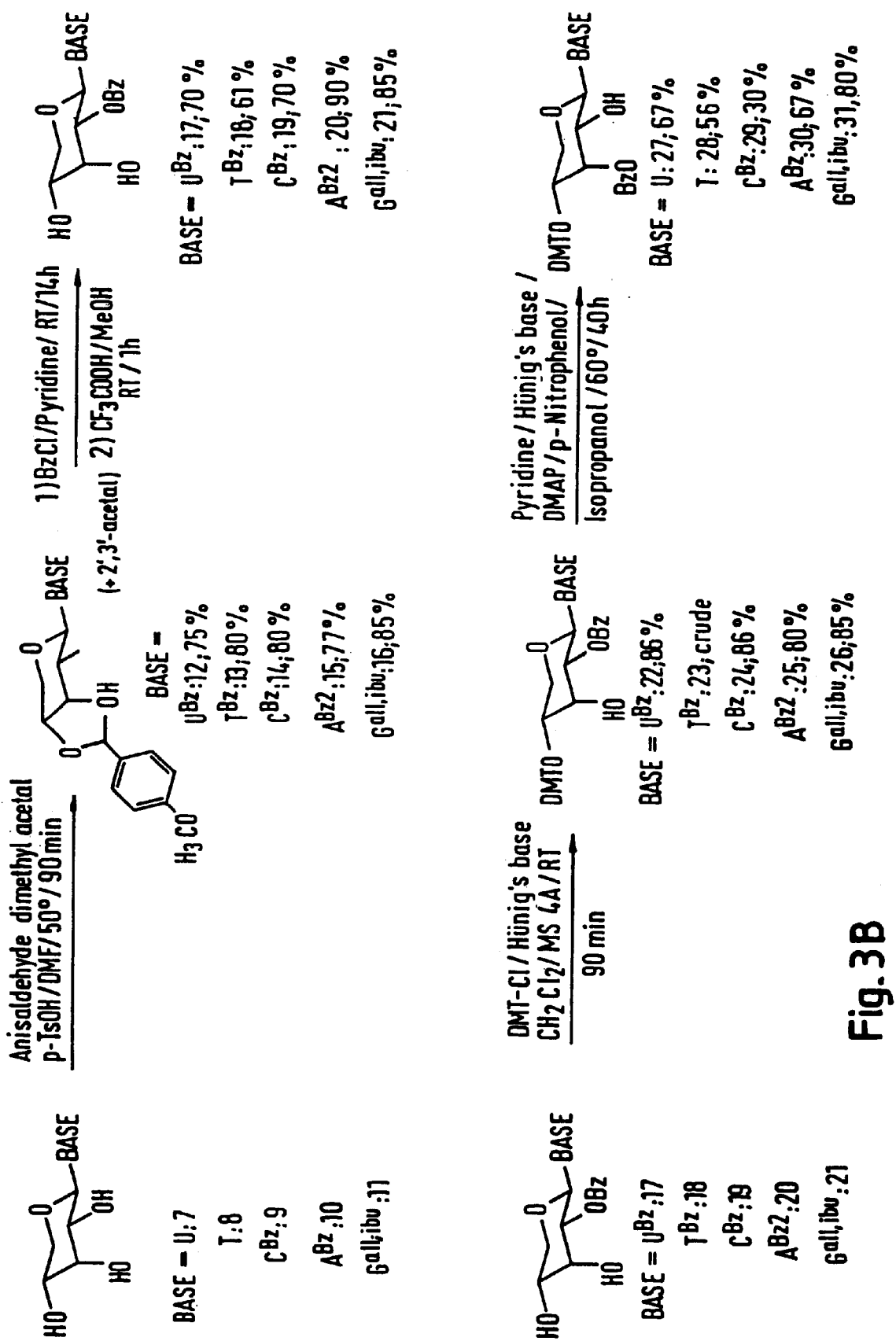
FIG. 3B: A reaction scheme showing the preparation of a 3', 4'-protected pentopyranosyl nucleoside according to the invention, wherein the 3',4'-clclic acetal is produced under reduced pressure.
Figure 3C:
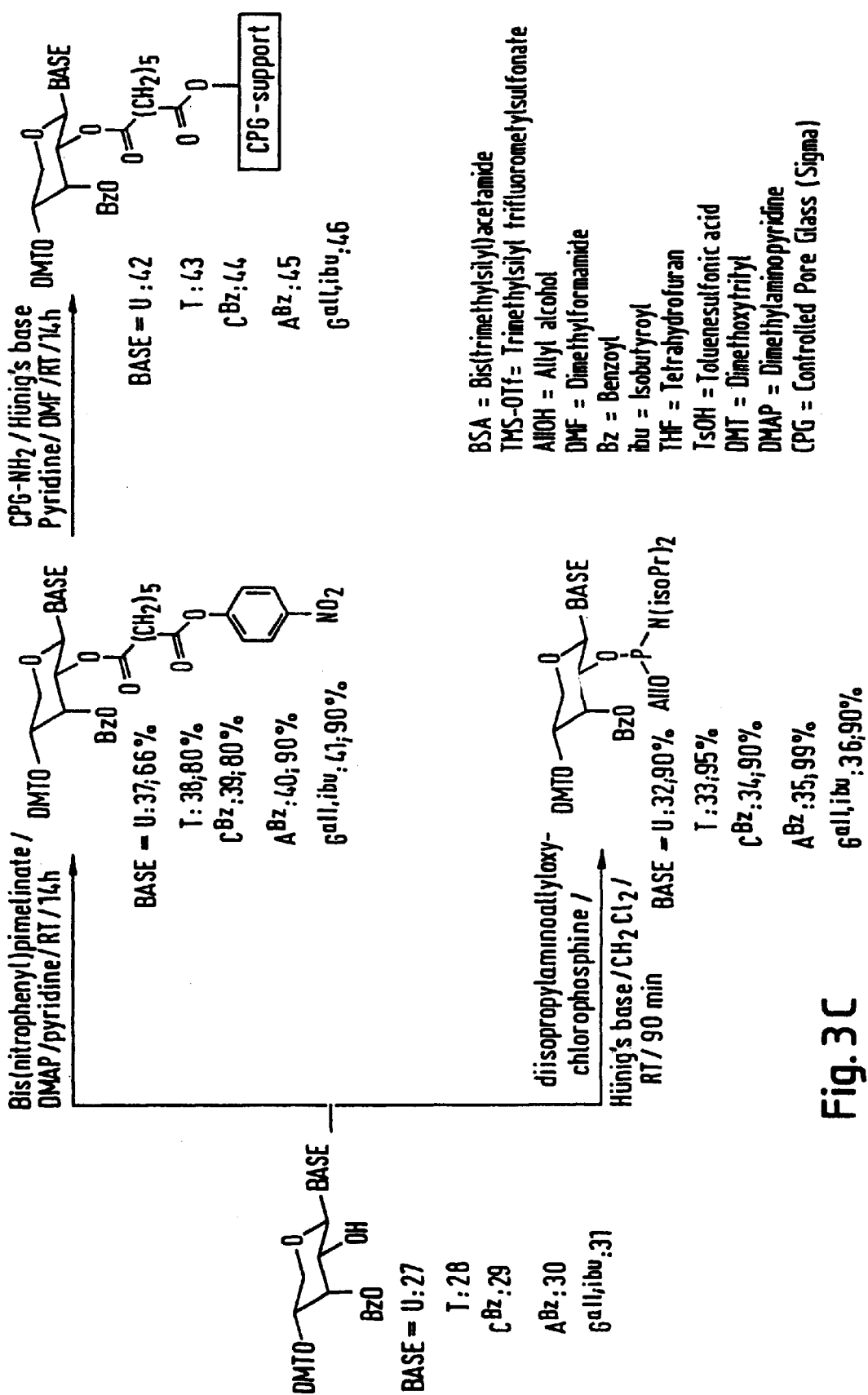
FIG. 3C: A reaction scheme showing the preparation of a pentopyranosyl nucleic acid, in which the pentopyranosyl nucleoside is either phosphitylated in a further step for oligomerization, or is bonded to a solid phase for solid-phase synthesis.

BSA means bis(trimethylsilyl)acetamide
TMS-OTf means trimethylsilyl trifluoromethylsulfonate
AllOH means allyl alcohol
DMF means dimethylformamide
Bz means benzoyl
ibu means isobutyryl
THF means tetrahydrofluran
TsOH means toluenesulfonic acid
DMT means dimethoxytrityl
DMAP means dimethylaminopyridine
CPG means controlled pore glass

EXAMPLES

Synthesis of an Oligomer of the Sequence G$_3$CG$_3$C
Preparation:

The amount of phosphoramidites (320 μl/coupling step) needed for the synthesis of the planned sequence and the quantity of tetrazole mixture (650 μl/coupling step of a 0.35 M tetrazole/0.15 M p-nitrophenyltetrazole solution) needed were each weighed into a synthesizer vial and dried over KOH flakes (desiccator) for at least 14 hours in a high vacuum. The mixture was then dissolved in the required volume of CH$_3$CN and mixed with about 5 beads of activated molecular sieve 4 Å. The vials were sealed with a septum and stored at RT for at least a further 14 hours.

Synthesis:

The synthesis of the sequence on the DNA synthesizer (Pharmacia gene assembler) was carried out in principle as that of DNA oligonucleotides according to the standard conditions of the automatic equipment manufacturer PHARMACIA, D-Freiburg. In the synthesis, the last trityl group was left on the oligonucleotide (trityl on). The following alterations to the standard conditions were introduced:

1. The detritylation times were prolonged to 7 min.;
2. A 6% strength (instead of 3% strength) solution of dichloroacetic acid in dichloroethane was used;
3. The coupling time was prolonged to 30 min.

For the synthesis, the starting material used was 400 mg of a support loaded with p-ribo-C component (=10 μmol).

Deprotection:

After the synthesis, the support still in the cartridge was dried in vacuo (about 30 min.) and treated with a prepared solution of 60 mg (66 μmol) of tetrakis(triphenylphosphine) palladium(0), 60 mg of triphenylphosphine (225 μmol) and 60 mg (170 μmol) of diethylammonium hydrogencarbonate in 4.5 ml of CH$_2$Cl$_2$. The mixture was shaken at room temperature (RT) for 5 hours, then the support was filtered off and washed successively with 20 ml of CH$_2$Cl$_2$ and 25 ml of acetone. It was taken up in 4.5 ml of 0.1 M sodium N,N-diethyldi-thiocarbamate solution and allowed to stand at RT for 30 min. It was then again filtered off and washed successively with 10 ml of H$_2$O, 15 ml of acetone and 10 ml of EtOH.

The support was then taken up in 3.6 ml of H$_2$O/0.9 ml of hydrazine hydrate and circulated at 4° (cold room) by means of a motor for 30 hours. It was then chromatographed on 1×4 cm RP-C$_{18}$ silica gel. For this, the column material was suspended in CH$_3$CN and packed into a column (1×5 cm). It was conditioned with 50 ml of CH$_3$CN, 50 ml of 2% NEt$_3$ in CH$_3$CN and then with 50 ml of 0.1 M TEAB buffer. After this, the sample was applied in 0.1 M TEAB buffer; it was eluted with 50 ml of 0.1 M TEAB buffer, 30 ml of H$_2$O and then with $H_2O \rightarrow H_2O/CH_3CN$ 1:1. The products were detected by UV photometry. The product-containing fractions were evaporated, taken up in 15 ml of $H_2O/HCOOH$ 1:4, allowed to stand at RT for 15 min., evaporated, treated with 5 ml of $H_2O$, evaporated again and chromatographed on Sepak (Waters). For this, the cartridge was washed with 15 ml of $CH_3CN$ and then with 15 ml of 0.1 M TEAB buffer. The oligonucleotide-containing solution was applied in 0.1 M TEAB buffer; it was then eluted with 10 ml of 0.1 M TEAB buffer and then with an $H_2O/CH_3CN$ gradient (0→50%). 1.5 ml fractions were collected; these were analyzed in the UV.

The product-containing fractions were evaporated and purified by HPLC chromatography. The combined, product-containing fractions were desalted on Sepak, as described above. The product was stored in the frozen state as an aqueous solution (10 ml). A yield of 25% (=250 o.D.) resulted by UV spectroscopy.

Characterization:

HPLC: retention time 15.3 min. on an Aquapore RP-300, 7 μm, 220×4.6 mm, flow 1 ml/min.; buffer A: 0.1 M $NEt_3/0.1$ M AcOH (pH 7.0) in $H_2O$, buffer B: 0.1 M $NEt_3/0.1$ M AcOH (pH 7.0) in $H_2O/CH_3CN$ 1:4; gradient: 100% A→70% A/30% B. Detection 260 nm. UV: λmax: 257 nm. MALDI-TOF-MS: [M-1]calc=2617; [M-1]obs=2617.

It will be apparent to those skilled in the art that various modifications and variations can be made to the compositions and processes of this invention. Thus, it is intended that the present invention cover such modifications and variations, provided they come within the scope of the appended claims and their equivalents.

Priority application DE 198 15 901.4 filed Apr. 8, 1998 including the specification, drawings, claims and abstract, is hereby incorporated by reference. All publications cited herein are incorporated in their entireties by reference.

What is claimed is:

1. A process for the preparation of a 3',4'-cyclic acetal of a pentopyranosyl nucleoside, which comprises reacting a pentopyranosyl nucleoside with a member selected from the group consisting of aldehyde, ketone, acetal, or ketal under a reduced pressure of less than about 500 mbar.

2. The process as claimed in claim 1, wherein the aldehyde is selected from the group consisting of formaldehyde, acetaldehyde, benzaldehyde, and 4-methoxybenzaldehyde.

3. The process as claimed in claim 1, further comprising the preparatory step of purifying the pentopyranosyl nucleoside.

4. The process as claimed in claim 3, wherein the pentopyranosyl nucleoside is purified over $SiO_2$.

5. The process as claimed in claim 4, wherein the pentopyranosyl nucleoside employed is selected from the group consisting of a ribopyranosyl nucleoside, an arabinopyranosyl nucleoside, alyxopyranosyl nucleoside, and a xylopyranosyl nucleoside.

6. The process as claimed in claim 1, wherein the nucleobase of the pentopyranosyl nucleoside is selected from the group consisting of: -purine, -2,6-diaminopurine, -6-purinethiol, -pyridine, -pyrimidine, -adenine, -guanine, -isoguanine, -6-thioguanine, -xanthine, -hypoxanthine, -thymine, -cytosine, -isocytosine, -indole, -tryptamine, -N-phthaloyltryptamine, -uracil, -caffeine, -theobromine, -theophylline, -benzotriazole, and -acridine.

7. The process as claimed in claim 1, wherein the pentopyranosyl nucleoside has the general formula (I)

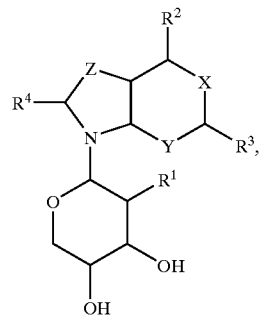

(I)

in which $R^1$ is equal to H, OH, Br, or Cl, $R^2$, $R^3$ and $R^4$ independently of one another, identically or differently, are each H, Br, Cl, $NR^5R^6$, $OR^7$, $SR^8$, =O, $C_nH_{2n+1}$ where n is an integer from 1–12, or $(C_nH_{2n})NR^{10}R^{11}$ where $R^{10}$ and $R^{11}$ are independently selected from H or $C_nH_{2n+1}$, or $R^{10}$ and $R^{11}$ are together a diradical of the formula

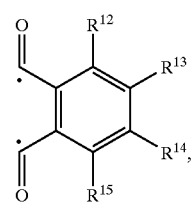

(III)

in which $R^{12}, R^{13}, R^{14}$ and $R^{15}$ independently of one another, identically or differently, in each case are H, $C_nH_{2n+1}$, $C_nH_{2n-1}$, or $OR^7$, where n is equal to an integer from 1–12, and $R^5$, $R^6$, $R^7$ and $R^8$ independently of one another, identically or differently, are in each case H, $C_nH_{2n+1}$, $C_nH_{2n-1}$, or $—C(O)R^9$ where $R^9$ is equal to a linear or branched, optionally substituted alkyl or aryl radical, and n is equal to an integer from 1–12, X, Y and Z independently of one another, identically or differently, are in each case =N—, =C($R^{16}$)— or —N($R^{17}$)— where $R^{16}$ and $R^{17}$ independently of one another, identically or differently, are in each case H or $C_nH_{2n+1}$ or $(CnH_{2n})NR^{10}R^{11}$, or the general formula (II)

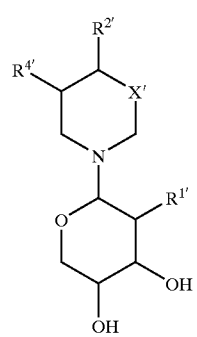

(II)

in which $R^{1'}$ is equal to H, OH, Br, or Cl, $R^{2'}$, $R^{3'}$ and $R^{4'}$ independently of one another, identically or differently, are in each case H, Br, Cl, =O, $C_nH_{2n+1}$, $OC_nH_{2n-1}$, or $(C_nH_{2n})NR^{10'}R^{11'}$, where $R^{10'}$, $R^{11'}$, independently of one another, have the above mentioned meaning of $R^{10}$ and $R^{11}$, and X' in each case is =N—, =C($R^{16'}$)— or —N($R^{17'}$)—, where $R^{16'}$ and $R^{17'}$ independently of one another have the above mentioned meaning of $R^{16}$ and $R^{17}$.

8. The process as claimed in claim 7, wherein $R^9$ is a phenyl radical.

9. The process as claimed in claim 1, wherein the reaction is carried out at a temperature of about 40–70° C.

10. The process as claimed in claim 1, wherein the reaction is carried out in the presence of an acid.

11. The process as claimed in claim 10, wherein the acid is selected from the group consisting of p-toluenesulfonic acid, methanesulfonic acid, tetrafluoroboric acid, sulfuric acid, acidic ion exchangers, and Lewis acids.

12. The process as claimed in claim 1, further comprising protecting the 3',4'-cyclic acetal of the pentopyranosyl nucleoside in the 2' position.

13. The process as claimed in claim 12, wherein the 2' position is protected by a protective group that is base-labile or is removable by metal catalysis.

14. The process as claimed in claim 12, further comprising deketalizing the 3',4'-cyclic acetal of the pentopyranosyl nucleoside that is protected in the 2' position.

15. The process as claimed in claim 14, wherein the deketalization is carried out in the presence of an acid.

16. The process as claimed in claim 14, wherein the reaction product obtained is worked up under dry basic conditions.

17. The process as claimed in claim 16, wherein the dry basic work-up is carried out in the presence of a member of the group consisting of solid hydrogen carbonate, carbonate, and basic ion exchanger.

18. The process as claimed in claim 14, further comprising protecting the 4'position after the deketalization.

19. The process as claimed in claim 18, wherein the 4' position is protected by a member of the group consisting of an acid-labile protective group, a base-labile protective group, and a β-eliminable group.

20. The process as claimed in claim 18, further comprising rearranging the protective group from the 2' position to the 3' position.

21. The process as claimed in claim 20, wherein the rearrangement is carried out in the presence of a base.

22. The process as claimed in claim 1, further comprising the preparatory steps of:

(a) reacting a protected nucleobase with a protected pentopyranose; and (b) removing the protective groups from the pentopyranosyl moiety of the product from step (a).

23. The process as claimed in claim 20, further comprising phosphitylating the pentopyranosyl nucleoside or bonding the pentopyranosyl nucleoside to a solid phase.

24. The process as claimed in claim 1, wherein the reduced pressure is less than about 100 mbar.

25. The process as claimed in claim 1, wherein the reduced pressure is less than about 50 mbar.

26. The process as claimed in claim 1, wherein the reduced pressure is about 30 mbar.

27. The process as claimed in claim 1, wherein the reaction is carried out at a temperature of about 50° C.–60° C.

28. The process as claimed in claim 1, wherein the reaction is carried out at a temperature of about 50° C.–60° C.

29. The process as claimed in claim 1 wherein the acetal is selected from the group consisting of formaldehyde dimethyl acetal, acetaldehyde dimethyl acetal, benzaldehyde dimethyl acetal, and 4-methoxybenzaldehyde dimethyl acetal.

30. The process as claimed in claim 1 wherein the ketone is selected from the group consisting of acetone, cyclopentanone, and cyclohexanone.

31. The process as claimed in claim 1 wherein the ketal is selected from the group consisting of acetone dimethyl ketal, cyclopentanone dimethyl ketal, cyclohexanone dimethyl ketal, and cyclohexanone 2-methoxypropene ketal.

* * * * *